(12) United States Patent
Lo et al.

(10) Patent No.: US 6,575,014 B2
(45) Date of Patent: Jun. 10, 2003

(54) SILICON MICRO-MACHINED FIXED-VOLUME BACK-FLUSH INJECTOR HAVING NO UNSWEPT DEAD VOLUME DURING INJECTION

(75) Inventors: Chi K. Lo, Hockessin, DE (US); Tak K. Wang, Havertown, PA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/870,779

(22) Filed: Jun. 1, 2001

(65) Prior Publication Data

US 2002/0178785 A1 Dec. 5, 2002

(51) Int. Cl.[7] .................. G01N 30/00; G01N 30/12; G01N 30/20
(52) U.S. Cl. ............... 73/23.41; 73/23.42; 210/198.2; 95/89; 422/89
(58) Field of Search ............ 73/23.42, 23.41, 73/23.35; 210/198.2; 95/82, 89; 422/89; 239/112

(56) References Cited

U.S. PATENT DOCUMENTS

| | | | | |
|---|---|---|---|---|
| 4,474,889 A | * | 10/1984 | Terry et al. ............... 436/161 |
| 5,347,844 A | * | 9/1994 | Grob et al. ................ 73/23.41 |
| 5,437,179 A | * | 8/1995 | Wiegand et al. ........... 75/23.35 |
| 5,449,902 A | * | 9/1995 | Onishi et al. ............... 250/288 |
| 5,487,313 A | * | 1/1996 | Johnson .................... 73/863.71 |
| 5,565,172 A | * | 10/1996 | Capuano et al. .............. 422/83 |
| 5,567,868 A | * | 10/1996 | Craig et al. ................ 73/23.42 |
| 5,583,281 A | * | 12/1996 | Yu ............................. 73/23.42 |
| 5,589,630 A | * | 12/1996 | Wiegand et al. ........... 73/23.35 |
| 5,601,785 A | * | 2/1997 | Higdon ........................ 422/103 |
| 5,652,398 A | | 7/1997 | Johnson .................... 73/863.71 |
| 6,156,197 A | * | 12/2000 | Dessapt et al. ........... 210/198.2 |
| 6,224,762 B1 | * | 5/2001 | Ferschneider et al. ... 210/198.2 |
| 6,395,560 B1 | * | 5/2002 | Markelov .................... 436/181 |
| 6,397,660 B1 | * | 6/2002 | Kikuchi et al. ............ 73/23.42 |

* cited by examiner

Primary Examiner—Helen Kwok
Assistant Examiner—David J. Wiggins

(57) ABSTRACT

A micro-machined back-flush injector that allows for a sample introduced into the injector to be properly injected into a gas chromatography apparatus in a short time period of between 10 and 100 milliseconds. A micro-machined injector having back-flushing capability that allows back-purging of unwanted components in the device and provides clean-up of channels in contact with the sample. Further, a method of operating an injector such that a sample is properly injected and purged from the system to which the injector is operably attached.

20 Claims, 5 Drawing Sheets

SILICON MICRO-MACHINED FIXED-VOLUME BACK-FLUSH INJECTOR HAVING NO UNSWEPT DEAD VOLUME DURING INJECTION

BACKGROUND OF THE INVENTION

1. Field of the Invention

The present invention relates generally to micro-machined back-flush injectors for gas chromatography. The present invention also relates to methods for manufacturing and operating micro-machined back-flush injectors.

2. Description of the Related Art

FIG. 1 illustrates a back-flush injector 10 according to the related art. The injector 10 includes a carrier gas inlet 20 connected to a main carrier gas loop 30 that is terminated at a fore-flush valve 35.

Off-shooting from the main carrier gas loop 30 is a reference column loop 40 that terminates at a reference column inlet 50. Also, off-shooting from the main carrier gas loop 30 is a pre-column back-flush loop 60 that terminates at a back-flush valve 70. A gas chromatography reference column (not shown) is positioned external to the injector 10 and operably connected to the reference column inlet 50. The reference column, typically used in conjunction with a thermal conductivity detector (not shown), enhances the detector signal and the overall sensitivity of the gas chromatography system.

The back-flush valve 70 is connected to an analytical column inlet channel 80 and a pre-column outlet channel 85. The analytical column inlet channel 80 leads to a gas chromatography analytical column (not shown) that is positioned externally to the injector 10. The pre-column outlet channel 85 leads to a pre-column (not shown) that will be discussed below.

A sample inlet 90 is also illustrated in FIG. 1. The sample inlet 90 is connected to an inlet channel 100 that, in turn, is connected to a sample valve 110. The sample valve 110 connects the inlet channel 100 to a dead volume channel 120 that extends to an injection valve 130.

One function of the injection valve 130 is to control flow between a pre-column inlet channel 135, that connects to the pre-column discussed above, and a fixed sample loop 140, that extends to the fore-flush valve 35. The fore-flush valve 35 regulates flow between the main carrier gas loop 30, the fixed sample loop 140, and a sample chamber 150. The back-flush valve 70 controls flow from the pre-column back-flush loop 60 into the analytical column inlet channel 80 and the pre-column outlet channel 85. The functions of these valves will be elaborated upon further when the operation of the injector 10 is discussed.

The sample chamber 150 terminates at a sample chamber outlet 160 that itself is connected to a switch solenoid 170, which is external to the injector 10. The switch solenoid 170 can either be opened to a carrier gas pressure source 180 or a pump 190 that leads to a vent 200. The pressure of gas in the carrier gas pressure source 180 is approximately the same as the pressure of the gas at the carrier gas inlet 20. The carrier gas pressure source 180, when allowed by the switch solenoid 170 to be connected to the sample chamber outlet 160, delivers carrier gas into the injector 10.

During gas chromatography analysis, a carrier gas at a regulated gas pressure is delivered by an outside source to the injector 10 through the gas carrier inlet 20. This carrier gas fills the main carrier gas loop 30, the reference column loop 40 and the pre-column back-flush loop 60. Carrier gas from the same outside source is also delivered to the carrier gas pressure source 180.

During operation, the injector 10 injects a gaseous sample to be analyzed via gas chromatography through the pre-column and analytical column discussed above. In order to properly inject the sample, the injector 10 uses five stages of operation. These stages include sampling, dwelling, sample compression, injection, and back-flushing.

During the operation of gas chromatograph and of the injector 10, a carrier gas such as, but not limited to, helium, hydrogen and argon, is delivered into the injector 10 through the carrier gas inlet 20 and fills the main carrier gas loop 30, the reference column loop 40 and the pre-column back-flush loop 60. The fore-flush valve 35 does not allow the carrier gas to flow into the fixed sample loop 140 or the sample chamber 150. The reference column inlet 50 allows some carrier gas to flow into the reference column. The carrier gas that enters the reference column does not return to the injector 10.

The back-flush valve 70 is also normally open during the idling stage (before the sample is introduced into the injector 10) and allows the carrier gas in the pre-column back-flush loop 60 to enter and fill the analytical column inlet channel 80 and the pre-column outlet channel 85. However, whether the back-flush carrier gas can travel into the fixed sample loop 140 is dependent on the status of the injection valve 130. When the injection valve 130 is open to the pre-column inlet channel 135, the carrier gas can then be delivered to the fixed sample loop 140 and the sample chamber 150. This flow is known as back-flushing.

The injector 10 can be set to allow back-flushing in the idling stage or can be set to not conduct back-flushing in order to reduce the consumption of the carrier gas. The carrier gas flow that passes through the analytical column inlet channel 80 proceeds to enter the analytical column, passes the detector (not shown), and does not return to the injector 10.

During the sampling stage, the sample valve 110 is opened and the pump 190 starts. Alternately, the pump 190 can be started earlier and the sample valve 110 can be opened subsequently. As another alternative, if the sample stream has a positive pressure, use of the pump 190 may not be needed.

Regardless of the alternative chosen, an inflow of gaseous sample from the sample inlet 90 enters and fills the inlet channel 100, passes through the sample valve 110 and fills the dead volume channel 120. The injection valve 130 allows the sample to fill the fixed sample loop 140 but does not allow flow of the sample into the pre-column inlet channel 135.

After the gaseous sample has moved through the fixed sample loop 140, it does not enter into the main carrier gas loop 30 because the fore-flush valve 35 is closed to this path. The sample can only travel into the sample chamber 150 and exits the injector 10 via the sample chamber outlet 160. Further, because the switch solenoid 170 is opened to the pump 190 during the sampling stage, the sample then travels through the pump 190 and exits the gas chromatographic instrument via the vent 200.

After the sampling stage, the sample valve 110 closes and the pump 190 stops drawing the sample into the injector 10. After approximately 100–500 milliseconds, the sample pressure in the fixed sample loop 140 and sample chamber 150 are set to be in equilibrium with the ambient pressure. This is known as the dwelling stage. Sample compression then follows.

During the compression stage, the switch solenoid 170 is actuated to open to the carrier gas pressure source 180 and a stream of carrier gas is delivered to the sample chamber 150 via the sample chamber outlet 160. Since the carrier gas has a higher pressure than the sample which has been set to be at ambient pressure during the dwelling stage, the carrier gas compresses the sample toward the fore-flush valve 35, the fixed sample loop 140, the injection valve 130, the dead volume channel 120, and the sample valve 110. Furthermore, during the compression stage, the fore-flush valve 35 does not allow the compressing sample to enter the main carrier gas loop 30.

During the injection stage, the injection valve 130 allows flow of the sample into the pre-column inlet channel 135. Also, the fore-flush valve 35 allows carrier gas from the carrier gas inlet 20 to travel from the main carrier gas loop 30 into the fixed sample loop 140 and sample chamber 150. However, since carrier gas from the carrier gas pressure source 180 is still compressing the sample, the only direction in which the carrier gas from the main carrier gas loop 30 can move is in one which forces the sample that was in the fixed sample loop 140 to enter the pre-column inlet channel 135 and, ultimately, the pre-column.

Also, during injection, the back-flush valve 70 closes and stops the back-flushing carrier gas in the pre-column back-flush loop 60 from entering into the analytical column inlet channel 80 and the pre-column outlet channel 85. This reduces resistance to the injection stream from the fore-flush valve 35 and the main carrier gas loop 30.

After the sample has entered and traveled through the pre-column, the sample re-enters the injector 10 through the pre-column outlet channel 85. Because the back-flush valve 70, during the injection stage, is positioned to allow the sample to flow from the pre-column outlet channel 85 to the analytical column inlet channel 80, the sample continues into the analytical column where the gas chromatographic analysis is conducted.

The above-described injection or fore-flushing stage typically takes several seconds to finish, depending on the particular gas chromatographic analysis undertaken. According to one type of analysis, all components of a sample to be analyzed are moved by the carrier gas towards the analytical column. However, during the movement of the components in the pre-column, some components may travel faster and some may be slower. Hence, the injection or fore-flushing time is selected to allow those components that are important to the analysis to move into the analytical column while leaving behind unimportant components in the pre-column.

During the back-flushing stage, which follows the fore-flushing stage, the unimportant components are purged away from the injector 10 so that they do not interfere with the analysis. In order to properly back-flush or "purge" all residual sample components in the pre-column from the injector 10, the back-flush valve 70 is opened to allow carrier gas from the pre-column back-flush loop 60 to flow into both the analytical column inlet channel 80 and the pre-column outlet channel 85. This causes carrier gas from the carrier gas inlet 20 to back-flush the pre-column on one hand, and to continue to move the components of interest into the analytical column, through the analytical column and towards the detector.

Once the back-flushing carrier gas passes through the pre-column, the carrier gas travels through the pre-column inlet channel 135 and flows out of the injection valve 130, through the fixed sample loop 140, through the fore-flush valve 35 and into the sample chamber 150. Because the switch solenoid 170 is open to the pump 190 during the back-flushing stage, the back-flushing carrier gas and any residual sample pushed by the carrier gas is released through the vent 200.

As can be seen from FIG. 1, a short-coming of the related art injector 10 illustrated has to do with the fact that there is sample trapped in the dead volume channel 120 during the injection process. To understand the problem that the trapped sample presents, one must take into account that the injection carrier gas from the fore-flush valve 35 only takes a small fraction of a second (10–100 millisecond) to move all sample in the fixed sample loop 140 into the pre-column inlet channel 135. The rest of the injection time or fore-flushing is supposed to have only 'pure' carrier gas flowing.

However, as there is no physical partition between the dead volume channel 120 and the fixed sample loop 140, the sample in the dead volume channel 120 continuously diffuses into the moving carrier gas stream and get 'injected', trace amount by trace amount, into the pre-column and the rest of the device. Since sample components with higher volatility and concentration diffuse faster, the chromatograms of these components are interfered with and unwanted shoulders 33 are found on the gas chromatographic peaks obtained during analysis, as illustrated in the chromatogram shown in FIG. 2.

Hence, what is needed is a back-flush injector 10 that allows for all of the sample introduced into the injector 10 to be properly injected into the pre-column and analytical column.

What is also needed is an injector 10 that is capable of back-flushing all of the sample remnant in the injector 10 after sample components of analytical concern have entered the analytical column.

BRIEF SUMMARY OF THE INVENTION

According to one embodiment, a micro-machined back-flush injector that includes a sample inlet, an analytical column inlet channel, and a plurality of channels that connect the sample inlet and the analytical column inlet channel, wherein the plurality of channels include a fixed sample loop connecting a sample valve and a fore-flush valve in the injector.

According to another embodiment, a method of operating a back-flush injector that includes introducing a sample into the injector, injecting the sample into an analytical device, and purging substantially all of the sample from the injector.

BRIEF DESCRIPTION OF THE DRAWINGS

The invention will be described by way of example, in the description of exemplary embodiments, with particular reference to the accompanying drawings in which.

DETAILED DESCRIPTION OF THE INVENTION

Figure 3:
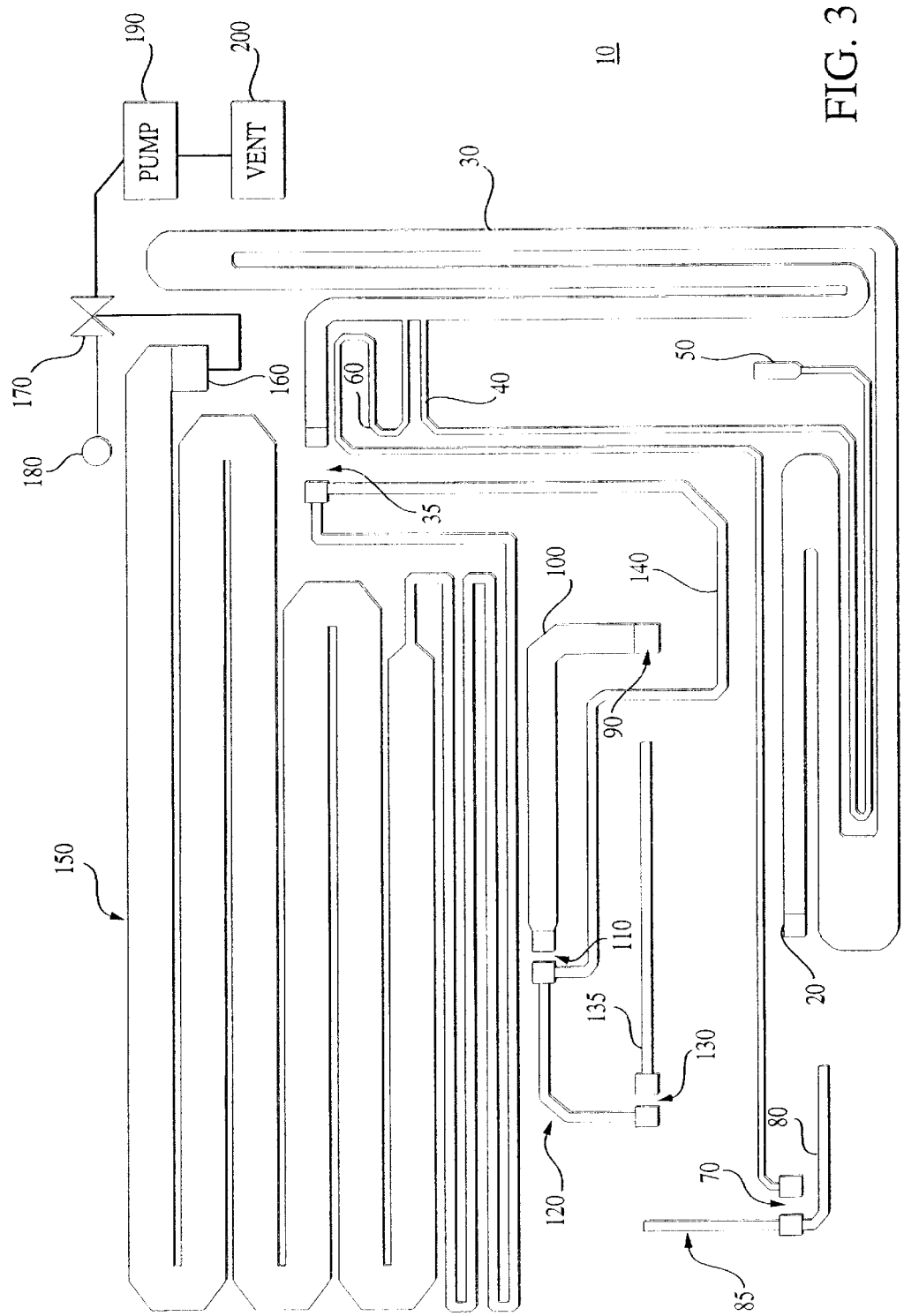
FIG. 3 illustrates one embodiment of a micro-machined, fixed-volume, back-flush injector according to the present invention.

FIG. 3 illustrates one embodiment of a micro-machined back-flush injector 10 according to the present invention. As shown in FIG. 3, the fixed sample loop 140 is positioned between the fore-flush valve 35 and the sample valve 110. Hence, although the injector 10 shown in FIG. 3 undergoes the sampling, dwell, sample compression, injection, and back-flushing stages described above, the configuration of the injector 10 carries out these stages in a more efficient manner.

During the idling stage of the instrument and injector 10, carrier gas enters through the carrier gas inlet 20 and fills the main carrier gas loop 30, the reference column loop 40, the pre-column back-flush loop 60 and the analytical column inlet channel 80. When sampling starts, the pump 190 starts. Then, the sample valve 110 is opened, the sample to be analyzed enters the injector 10 through the sample inlet 90 and the sample fills the inlet channel 100.

Once the sample reaches the sample valve 110 at the end of the inlet channel 100, a small portion of the sample fills the dead volume channel 120. However, this portion of the sample cannot flow into the pre-column inlet channel 135 because the injection valve 130 is closed. The rest of the sample flows through the fixed sample loop 140, through the fore-flush valve 35, into the sample chamber 150, and out through the vent 200 via the switch solenoid 170 that is open to the pump 190. The fore-flush valve 35 does not allow the sample to flow into the main carrier gas loop 30.

The closure of the sample valve 110 and the shutting off of the pump 190, if it is used, end the sampling stage and start the dwell stage that helps to equilibrate the sample pressure to that of the ambient pressure. The dwell stage takes about 100–500 milliseconds.

During the sample compression stage, the switch solenoid 170 is opened to the carrier gas pressure source 180 that delivers carrier gas into the sample chamber 150 through the sample chamber outlet 160. The carrier gas from the carrier gas pressure source 180 compresses the sample in a portion of the sample chamber 150, in the fixed sample loop 140, and in the dead volume channel 120 towards the injection valve 130. During the compression state, the sample valve 110 does not allow flow of the sample into the sample inlet channel 100.

During the injection stage, the fore-flush valve 35 allows carrier gas in the main carrier gas loop 30 to flow into the sample chamber 150 and into the fixed sample loop 140. The carrier gas that flows from the main carrier gas loop 30 into the fixed sample loop 140 pushes the sample in the fixed sample loop 140 towards the now-open injection valve 130. Because the injection valve 130 is opened during the injection stage, the sample in the fixed sample loop 140 travels through the sample valve 110, through the dead volume channel 120, and into the pre-column inlet channel 135. The sample then flows through the pre-column and pre-column outlet channel 85.

When injection or fore-flushing starts, the back-flush valve 70 closes and ceases to deliver carrier gas to the analytical column inlet channel 80 and the pre-column outlet channel 85. This minimizes resistance to the inflow of sample in the fixed sample loop 140 into the injection valve 130, the pre-column and the rest of the device. It is important to note that, during this stage, all sample from the fore-flush valve 35 to the injection valve 130 is injected into the pre-column in a short instant, leaving no residual sample that can escape into the pre-column during the rest of the analytical process.

The injection stage or fore-flushing takes several seconds, depending on the particular gas chromatographic analysis performed. Back-flushing then follows.

During the back-flushing stage of operation, the back-flush valve 70 allows carrier gas in the pre-column back-flush loop 60 to flow both into the analytical column inlet channel 80 and into the pre-column outlet channel 85. The back-flushing carrier gas travels through the pre-column, the pre-column inlet channel 135, the injection valve 130, the dead volume channel 120 and the fixed sample loop 140. The carrier gas effectively pushes any remaining sample through the fore-flush valve 35, out of the sample chamber 150 and, because the switch solenoid 170 is opened to the pump 190 during the back-flushing stage, out through the vent 200. The carrier gas flow in the direction of the analytical column will continue to move the captured components towards the detector and, during the movement, the components are further separated by the analytical column.

Figure 4:
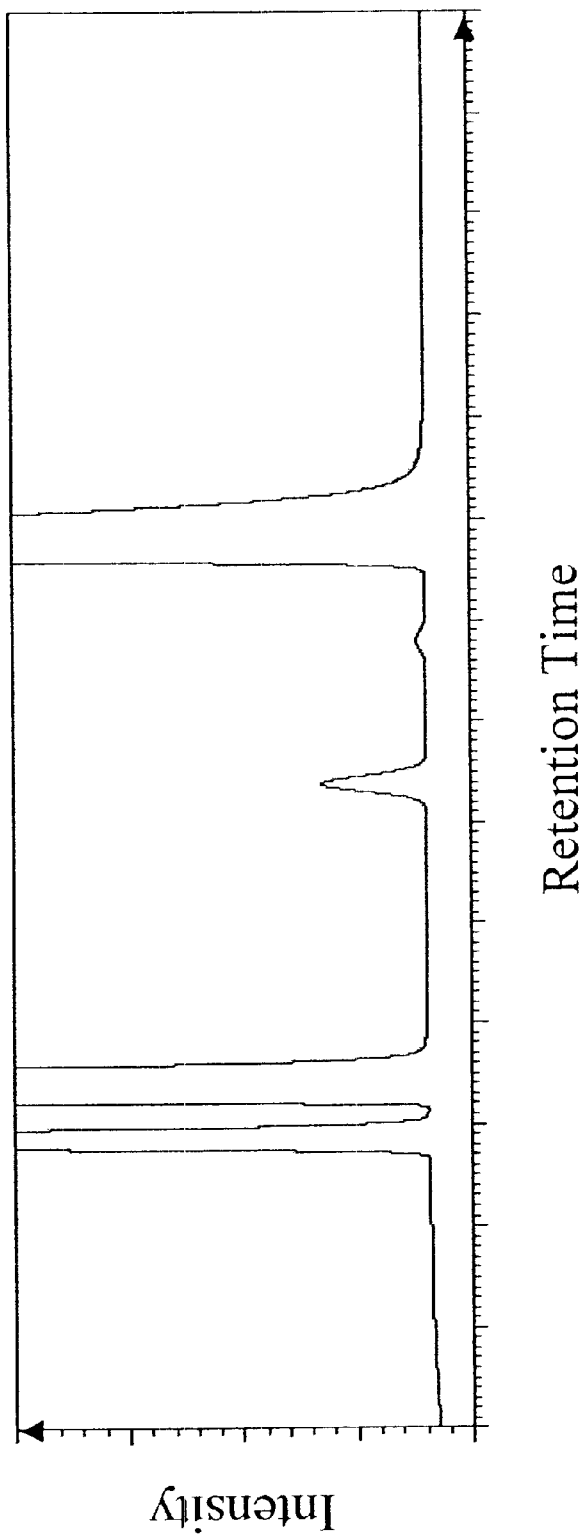
FIG. 4 is a gas chromatogram of a sample analyzed using a back-flush injector according to an embodiment of the present invention wherein no shoulders are present adjacent to the main peaks of the sample.

According to the processes described above, no appreciable amount of sample remains in the dead volume channel 120 during the injection process. Hence, as is seen in FIG. 4, a chromatogram of a sample analyzed via gas chromatography using the injector 10 illustrated in FIG. 4 shows no shoulders 33 on the sides of the peaks. Further, during back-flushing of the injector 10, carrier gas will clean up all channels that have been in contact with the sample. This minimizes sample carry-over to future gas chromatography analyses that will be performed on other samples using the same apparatus.

Figure 1:
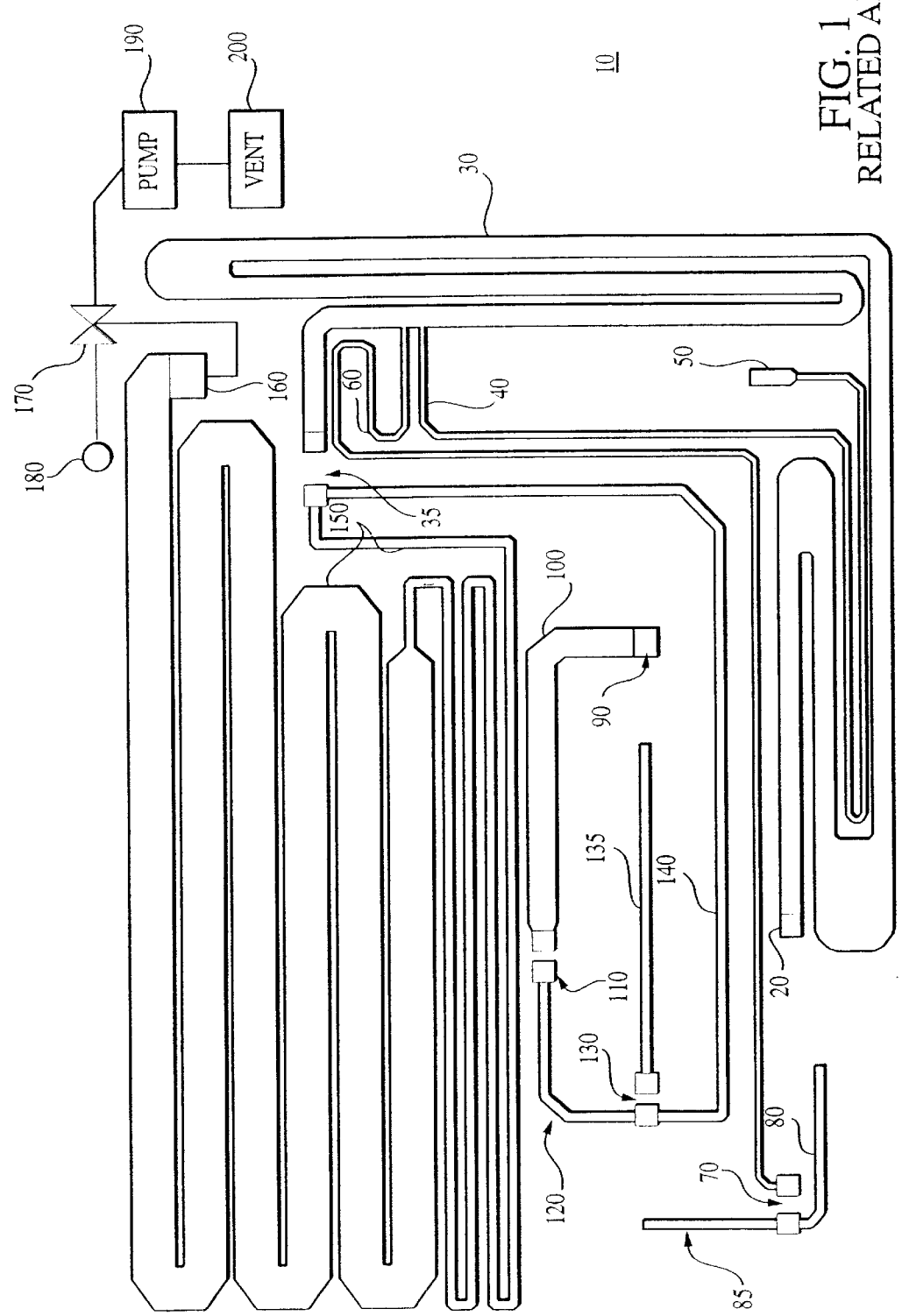
FIG. 1 illustrates a silicon, micro-machined, fixed-volume, back-flush injector according to the related art.
Figure 2:
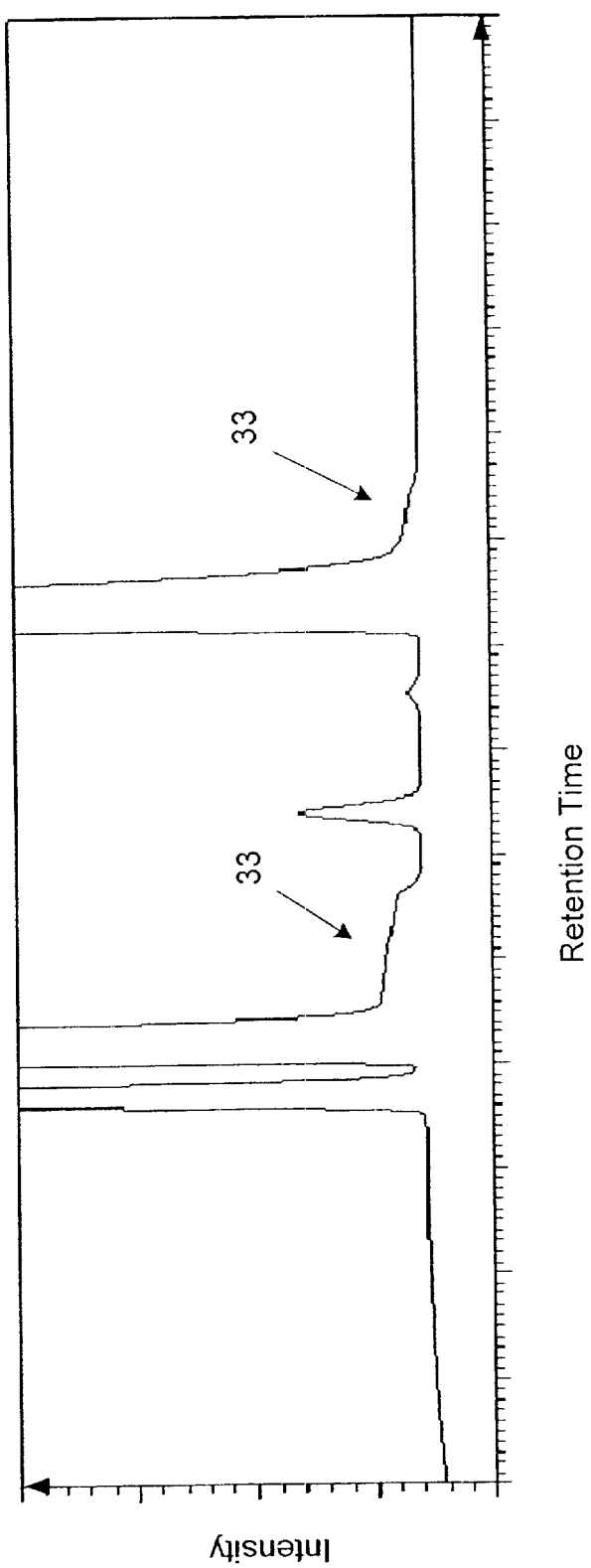
FIG. 2 is a gas chromatogram of a sample analyzed using a back-flush injector according to the related art wherein shoulders are present adjacent to the main peaks of the sample.

In other words, when using the injector 10 illustrated in FIG. 3, carrier gas typically pushes the sample completely into the analytical column in a short instant (below 100 msec) during the injection stage and leaves no residual sample that can escape into the pre-column during the rest of the injection or fore-flushing time. During the back-flushing stage, the carrier gas pushes residual sample that might be present in the sample chamber 150 out of the injector 10 and cleans up all channels previously in contact with the sample flow. Hence, the chromatograph shoulders 33 and sample residue shortcomings of the injector 10 according to the related art, as illustrated in FIG. 1, are avoided.

Figure 5:
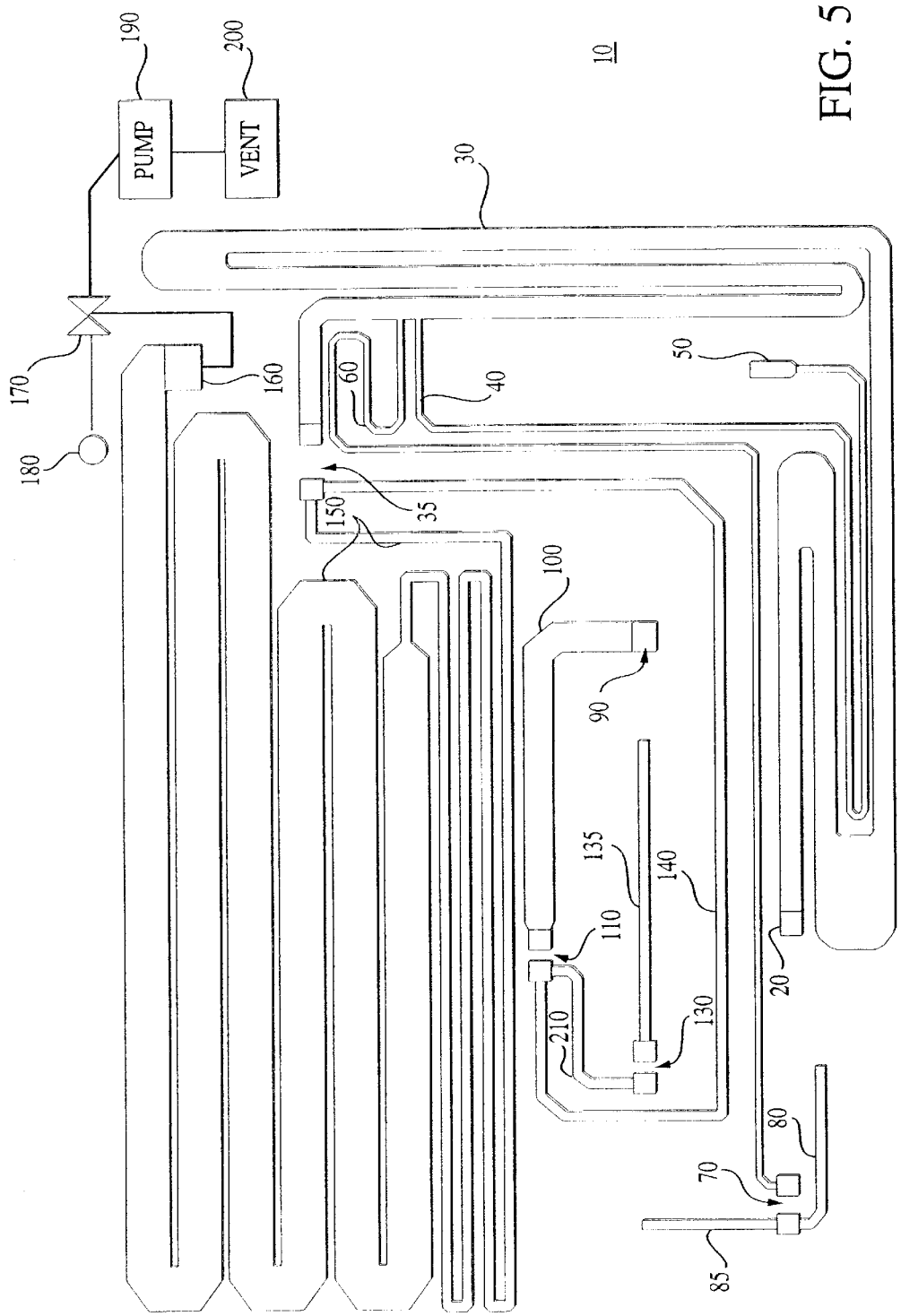
FIG. 5 illustrates another embodiment of a micro-machined, fixed-volume, back-flush injector according to the present invention.

FIG. 5 illustrates yet another embodiment of the present invention wherein an added channel 210, that should be, according to certain embodiments, as short as possible, connects the sample valve 110 and the injection valve 130. The "dead volume" channel 120 now is part of the fixed loop 140 and detached from the injection valve 130. According to this embodiment, carrier gas can also push the sample quickly and completely into the pre-column during the injection stage while leaving no residual sample. Further, the back-flushing stage ensures that the carrier gas removes residual sample out of the injector 10 and allows subsequent chromatography analyses to be conducted using the same apparatus.

More specifically, the sample that enters the injector illustrated in FIG. 5 is allowed, by proper opening and shutting of valves, to fill the fixed loop 140 and the added channel 210. During sampling, the sample valve 110 allows sample flow from the sample inlet channel 100 into the fixed loop 140. The injection valve 130 is also closed to the added channel 210 during this stage.

When injecting sample, the injection valve 130 is opened and carrier gas that flows through the fore-flush valve 35 forces sample in the fixed loop 140 and in the added channel 210 to flow into the pre-column inlet channel 135. This also ensures that no residual sample is allowed to diffuse from the dead volume channel 120.

When back-flushing the embodiment illustrated in FIG. 5, the valves are set such that carrier gas flows into the pre-column inlet channel 135, flows through the added channel 210 and forces all residual sample out of the injector 10 via the added channel 210. This allows for future analyses to be conducted on other samples, without residual interference, using the same apparatus.

The foregoing detailed description has been given for understanding exemplary implementations of the invention only and no unnecessary limitations should be understood therefrom as modifications will be obvious to those skilled in the art without departing from the scope of the appended claims and their equivalents.

What is claimed is:

1. A micro-machined back-flush injector comprising:
   a sample inlet;
   an analytical column inlet channel; and
   a plurality of channels that connect the sample inlet and the analytical column inlet channel, wherein the plurality of channels include a fixed sample loop connecting a sample valve and a fore-flush valve in the injector.

2. The micro-machined back-flush injector of claim 1, wherein the plurality of channels further comprise:
   an inlet channel connecting the sample inlet and the sample valve.

3. The micro-machined back-flush injector of claim 1, wherein the plurality of channels further comprise:
   a pre-column inlet channel connecting an injection valve and a pre-column.

4. The micro-machined back-flush injector of claim 1, wherein a dead volume channel comprises a channel along the shortest available path length between the sample valve and an injection valve.

5. The micro-machined back-flush injector of claim 1, wherein the plurality of channels further comprise:
   a main carrier gas loop connecting the fore-flush valve and a carrier gas inlet.

6. The micro-machined back-flush injector of claim 1, wherein the plurality of channels further comprise:
   a pre-column back-flush loop connecting a main carrier gas loop and a back-flush valve.

7. The micro-machined back-flush injector of claim 1, wherein the analytical column inlet channel connects a back-flush valve and an analytical column.

8. The micro-machined back-flush injector of claim 1, wherein the plurality of channels further comprise:
   a pre-column outlet channel connecting a back-flush valve and a pre-column.

9. A method of operating a back-flush injector comprising:
   introducing a sample into the injector;
   injecting the sample into an analytical device; and
   purging substantially all of the sample from the injector.

10. The method of claim 9, wherein the introducing step comprises:
    allowing the sample to fill an inlet channel, a dead volume channel, a fixed sample loop and a sample chamber of the injector.

11. The method of claim 9, wherein the introducing step comprises:
    filling a main carrier gas loop, a reference column back-flush loop, a pre-column back-flush loop and an analytical column inlet channel of the injector with carrier gas.

12. The method of claim 9, wherein the introducing step comprises opening a vacuum pump and subsequently opening a sampling valve.

13. The method of claim 9, further comprising compressing the sample.

14. The method of claim 13, wherein the compressing step comprises allowing carrier gas to flow into a sample chamber of the injector.

15. The method of claim 13, wherein the compressing step comprises compressing the sample into a sample chamber, a fixed sample loop and a dead volume channel.

16. The method of claim 9, wherein the injecting step comprises allowing the sample to flow into a pre-column inlet channel of the injector.

17. The method of claim 9, wherein the back-flushing step comprises allowing carrier gas to flow into a fixed sample loop, a dead volume channel and a pre-column inlet channel of the injector.

18. The method of claim 9, wherein the back-flushing step comprises allowing carrier gas to displace any sample in a pre-column.

19. A micro-machined back-flush injector comprising:
    a sample inlet;
    an analytical column inlet channel;
    a plurality of channels that connect the sample inlet and the analytical column inlet channel, wherein the plurality of channels include a fixed sample loop connecting a sample valve and a fore-flush valve in the injector; and
    a dead volume channel connecting the sample valve and an injection valve.

20. A method of operating a back-flush injector comprising:
    introducing a sample into the injector;
    injecting the sample into an analytical device;
    purging substantially all of the sample from the injector; and
    allowing a carrier gas to push the sample through a dead volume channel.

* * * * *